United States Patent [19]

Engelhardt et al.

[11] Patent Number: 4,619,927
[45] Date of Patent: Oct. 28, 1986

[54] NOVEL NITROPYRAZINYL- AND NITROPYRIDINYL- SUBSTITUTED PIPERAZIN-3-ONE AND HEXAHYDRO-1H-1,4-DIAZEPIN-5-ONE COMPOUNDS USEFUL AS ADJUNCTS TO RADIATION THERAPY

[75] Inventors: Edward L. Engelhardt, Gwynedd Valley; Walfred S. Saari, Lansdale, both of Pa.

[73] Assignee: Merck & Co., Inc., Rahway, N.J.

[21] Appl. No.: 716,884

[22] Filed: Mar. 27, 1985

[51] Int. Cl.$^4$ .................. A61K 31/55; A61K 31/495; C07D 401/04
[52] U.S. Cl. .................................. 514/218; 514/255; 544/359; 544/360; 540/492
[58] Field of Search ................. 260/239.3 R; 544/359, 544/360; 514/218, 255

[56] References Cited

U.S. PATENT DOCUMENTS

| | | | |
|---|---|---|---|
| 4,414,215 | 11/1983 | Hartman | 424/250 |
| 4,416,882 | 11/1983 | Hartman | 424/250 |
| 4,418,062 | 11/1983 | Hartman | 424/248.4 |
| 4,435,400 | 3/1984 | Hartman | 424/250 |
| 4,438,266 | 3/1984 | Hartman | 544/350 |

*Primary Examiner*—Robert T. Bond
*Attorney, Agent, or Firm*—Hesna J. Pfeiffer; Thomas E. Arther

[57] ABSTRACT

Novel nitropyrazinyl- and nitropyridinyl- substituted piperazin-3-one and hexahydro-1H-1,4-diazepin-5-one compounds are disclosed to have activity in increasing the sensitivity of hypoxic tumor cells to radiation. Also disclosed are methods of preparing such compounds and pharmaceutical compositions including such compounds.

7 Claims, No Drawings

NOVEL NITROPYRAZINYL- AND NITROPYRIDINYL- SUBSTITUTED PIPERAZIN-3-ONE AND HEXAHYDRO-1H-1,4-DIAZEPIN-5-ONE COMPOUNDS USEFUL AS ADJUNCTS TO RADIATION THERAPY

BACKGROUND OF THE INVENTION

This invention relates to nitropyrazinyl-and nitropyridinyl- substituted piperazin-3-one and hexahydro-1H-1,4-diazepin-5-one compounds used as sensitizers of hypoxic tumor cells to therapeutic radiation. It also relates to the process of preparing such compounds by reaction of substituted piperazin-3-one and hexahydro-1H-1,4-diazepin-5-one compounds with certain specific chloronitropyrazines and chloronitropyridines defined hereinbelow.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, but are believed to have a more favorable therapeutic ratio.

DETAILED DESCRIPTION OF THE INVENTION

The compounds of the present invention are represented by the general formula:

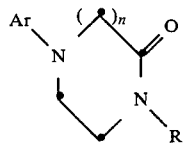

I wherein Ar is selected from the group consisting of 3-nitro-2-pyrazinyl and 3-nitro-4-pyridyl, R is selected from the group consisting of hydrogen and hydroxyethyl, and n is either 1 or 2.

The compounds of the present invention are prepared in the following manner:

A lactam of the formula:

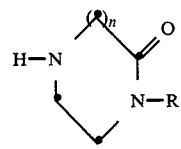

II wherein n is either 1 or 2 and;

R is hydrogen or hydroxyethyl is treated with 2-chloro-3-nitropyrazine or 4-chloro-3-nitropyridine in the presence of a base to produce compound I hereinabove.

The reaction is carried out in a suitable solvent such as a lower alcohol, a polar solvent such as dimethylformamide, dimethylsulfoxide, tetramethylurea, or others such as tetrahydrofuran, glyme, diglyme and pyridine.

A preferred solvent for this reaction is isopropyl alcohol.

The reaction mixture should also contain sufficient base to neutralize the hydrochloric acid formed during the reaction. This base may be in the form of an organic amine such as pyridine or triethylamine or inorganic base such as an alkali metal carbonate, bicarbonate or hydroxide with organic bases being preferred.

The temperature of the reaction is not critical and it is desirably maintained between 0° and 100° C. and preferably between 0° and 25° C. for a period of from 1–25 hours.

The method of treatment of human patients or domestic animals undergoing radiation treatment of malignant disease processes employs the compounds of the present invention in pharmaceutical compositions that are administered orally or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage of between 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each suceeding radiation treatment, observing the patient carefully for any drug side effect. The composition to be administered is an effective amount of the active compound and a pharmaceutical carrier for said active compound.

The dosage form for intravenous administration is a sterile isotonic solution. Oral dosage forms such as tablets, capsules, or elixirs are preferred.

Capsules or tablets containing 25, 50, 100 or 500 mg of drug/capsule or tablet are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLE 1

1-(3-Nitro-2-pyrazinyl)piperazin-3-one

A solution of 2-chloro-3-nitropyrazine (9.1 g, 57 mmol) in chloroform (100 ml) was added dropwise over 45 minutes to a cooled solution of piperazine-2-one (5.71 g, 57 mmol) and triethylamine (8.0 ml, 57 mmol) in isopropanol (120 ml). After addition was complete, the reaction mixture was allowed to warm to 20°–25° and was stirred at this temperature for 20 hours. The precipitate was removed by filtration and recrystallized from methanol-ethyl acetate-hexane to give 6.96 g (54.7%) of product, m.p. 178°–179°.

EXAMPLE 2

1-(3-Nitro-2-pyrazinyl)hexahydro-1H-1,4-diazepin-5-one

To a solution of hexahydro-1H-1,4-diazepin-5-one (1.14 g, 10 mmol) and triethylamine (1.01 g, 10 mmol) in isopropanol (30 ml) cooled in an ice bath, was added over 30 minutes a solution of 2-chloro-3-nitropyrazine (1.59 g, 10 mmol) in chloroform (20 ml). After addition was complete, the reaction mixture was allowed to warm to 20°–25° and was stirred at this temperature for 20 hours. Solvents were removed under reduced pressure and the residue was partitioned between a saturated aqueous solution of sodium chloride and ethyl acetate. The ethyl acetate extract was dried over anhydrous sodium sulfate, filtered and concentrated to an oil. Flash chromatography over silica gel and elution with 2% methanol −98% chloroform gave pure 1-(3-nitro-2-pyrazinyl)hexahydro-1H-1,4-diazepin-5-one.

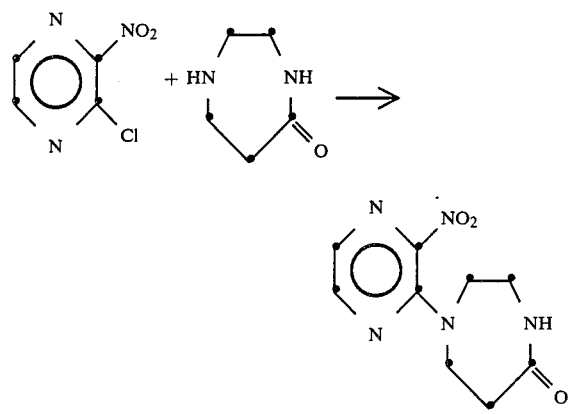

EXAMPLE 3

1-(3-Nitro-2-pyrazinyl)-4-(2-hydroxyethyl)piperazin-3-one)

Step A

1-Carbobenzoxy-4-(2-hydroxyethyl)piperazine-3-one

To a solution of 1-carbobenzoxypiperazin-3-one (234 mg, 1.0 mmol) in dimethylformamide (10 ml) under nitrogen was added in one portion, 50% sodium hydride (48 mg, 1 mmol). After stirring at 20°–25° for 30 minutes until all of the sodium hydride had reacted, a solution of 2-(2-bromoethoxy)-tetrahydropyran (209 mg, 1 mmol) in dimethylformamide (2 ml) was added and the reaction mixture stirred at 20°–25° for 20 hours. Solvent was removed at 40°–45° and 0.1 mm and the residue chromatographed over silica gel. Elution with 2% isopropanol −98% methylene chloride gave the pure protected alcohol as an oil.

The tetrahydropyranyl blocking group was removed by heating a solution of the protected alcohol (200 mg, 0.55 mmol) in a mixture of acetic acid (8 ml), tetrahydrofuran (4 ml) and water (2 ml) at 50° for 4 hours. After removing solvents under reduced pressure, the residue was partitioned between saturated sodium bicarbonate solution and ethyl acetate. The ethyl acetate extract was dried over anhydrous sodium sulfate, filtered and concentrated. Chromatography of the residue over silica gel and elution with 5% methanol-95% chloroform gave pure 1-carbobenzoxy-4-(2-hydroxyethyl)-piperazine-3-one.

Step B 4-(2-Hydroxyethyl)piperazin-3-one

A solution of 1-carbobenzoxy-4-(2-hydroxyethyl)piperazine-3-one (1.0 g, 35.9 mmol) in absolute ethanol (75 ml) was hydrogenated over a 10% palladium on carbon catalyst (1.0 g) at 20°–25° and an initial pressure of 40 psi for 6 hours. Catalyst was removed by filtration through diatomaceous earth and the filtrate concentrated under reduced pressure to give 4-(2-hydroxyethyl)piperazine-3-one.

Step C 1-(3-Nitro-2-pyrazinyl)-4-(2-hydroxyethyl)piperazin-3-one

A solution of 2-chloro-3-nitropyrazine (1.59 g, 10 mmol) in chloroform (20 ml) was added over 30 minutes to an icebath cooled solution of 4-(2-hydroxyethyl)piperazin-3-one (1.44 g, 10 mmol) and triethylamine (1.01 g, 10 mmol) in isopropanol (30 ml). After addition was complete, the reaction mixture was allowed to warm to 20°–25° and was stirred at this temperature for 20 hours. Solvents were removed under reduced pressure and the residue was partitioned between a saturated aqueous solution of sodium chloride and ethyl acetate. The ethyl acetate extract was dried over anhydrous sodium sulfate, filtered and concentrated to an oil. Flash chromatography over silica gel and elution with 5% methanol-95% chloroform gave 0.90 g (48.6%) of 1-(3-nitro-2-pyrazinyl)-4-(2-hydroxyethyl)piperazin- 3-one. An analytical sample, m.p. 117°–120°, was obtained upon recrystallization from ethyl acetatehexane.

EXAMPLE 4

1-(3-Nitro-4-pyridyl)piperazin-3-one

A solution of 4-chloro-3-nitropyridine (434 mg, 2.74 mmol) in 2 ml of dimethylformamide was added dropwise to a stirred suspension of 548 mg (5.47 mmol) of piperazin-2-one in 2 ml of dimethylformamide at room temperature (approximately 25°) over a period of 30 minutes. A voluminous bright yellow solid began to separate when about half of the solution had been added. After stirring at room temperature for 20 hours, the dimethylformamide was removed by passing a slow stream of nitrogen over the surface of the reaction mixture while heating in a bath at 80° for 18 hours. The yellow crystalline residue, with a small amount of dark brown material on the surface, was recrystallized from 5 ml of water to give 536 mg of product that sintered at 201° and decomposed at 204°. A second recrystallization from water, 27 ml, gave 453 mg of bright yellow needles, dec. 212°, with effervescence.

What is claimed is:

1. A compound of the formula

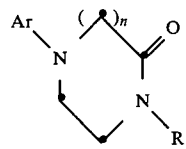

wherein n is 1 or 2 and R is hydrogen or hydroxyethyl; and Ar is an aryl group selected from 3-nitro-2-pyrazinyl and 3-nitro-4-pyridyl.

2. A method for enhancing the therapeutic effect of radiation which comprises administering to a patient in need of such radiation treatment an effective amount of a compound defined in claim 1.

3. A pharmaceutical composition for enhancing the therapeutic effect of radiation which contains an effective amount of a compound defined in claim 1 and a non-toxic pharmaceutically acceptable carrier.

4. A compound according to claim 1 which is 1-(3-nitro-2-pyrazinyl)piperazin-3-one.

5. A compound according to claim 1 which is 1-(3-nitro-2-pyrazinyl)hexahydro-1H-1,4-diazepin-5-one.

6. A compound according to claim 1 which is 1-(3-nitro-2-pyrazinyl)-4-(2-hydroxyethyl)piperazin-3-one.

7. A compound according to claim 1 which is 1-(3-nitro-4-pyridyl)piperazin-3-one.

* * * * *